United States Patent
Paek et al.

(10) Patent No.: US 10,093,597 B1
(45) Date of Patent: Oct. 9, 2018

(54) PROCESSES FOR SEPARATING DIMETHYL BIPHENYL ISOMERS USING ZEOLITE ADSORBENTS

(71) Applicant: ExxonMobil Research and Engineering Company, Annandale, NJ (US)

(72) Inventors: Changyub Paek, Bridgewater, NJ (US); Michael P. Lanci, Flemington, NJ (US); Randall D. Partridge, Califon, NJ (US); Allen W. Burton, Stewartsville, NJ (US); Peter I. Ravikovitch, Princeton, NJ (US); Sumathy Raman, Annandale, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 15/886,153

(22) Filed: Feb. 1, 2018

(51) Int. Cl.
| | |
|---|---|
| *C07C 7/12* | (2006.01) |
| *C07C 7/13* | (2006.01) |
| *B01J 20/28* | (2006.01) |
| *B01J 20/18* | (2006.01) |

(52) U.S. Cl.
CPC ........... *C07C 7/13* (2013.01); *B01J 20/18* (2013.01); *B01J 20/28071* (2013.01); *B01J 20/28073* (2013.01)

(58) Field of Classification Search
CPC .................................. C07C 7/12; C07C 7/13
USPC ........................................ 585/826, 827, 828
See application file for complete search history.

(56) References Cited

U.S. PATENT DOCUMENTS

| | | | |
|---|---|---|---|
| 3,626,020 A | 12/1971 | Neuzil | |
| 3,699,182 A | 10/1972 | Cattanach | |
| 5,202,516 A * | 4/1993 | Lee | B01J 29/18 585/467 |
| 6,730,625 B1 | 5/2004 | Chang et al. | |
| 8,580,120 B2 | 11/2013 | Porter | |
| 9,085,669 B2 | 7/2015 | Dakka et al. | |
| 9,328,053 B2 | 5/2016 | Bai et al. | |
| 9,580,572 B2 | 2/2017 | Dakka et al. | |
| 9,663,417 B2 | 5/2017 | Dakka et al. | |
| 9,688,602 B2 | 6/2017 | Dakka et al. | |
| 2009/0326310 A1 | 12/2009 | Kulprathipanja et al. | |
| 2016/0176785 A1 | 6/2016 | Salciccioli et al. | |

FOREIGN PATENT DOCUMENTS

| | | |
|---|---|---|
| WO | 2014117076 A1 | 7/2014 |
| WO | 2014117076 A9 | 7/2015 |
| WO | 2015112252 A1 | 7/2015 |
| WO | 20150191289 A1 | 12/2015 |

OTHER PUBLICATIONS

Baertsch et al., "Permeation of aromatic hydrocarbon vapors through silicalite-zeolite membranes", J. Phys. Chem., 1996, vol. 100, pp. 7676-7679.
Foster et al., "A geometric solution to the largest-free-sphere problem in zeolite frameworks", Micropo. Mesopor. Mat., 2006, vol. 90, pp. 32-38.
Funke et al., "Separation of close-boiling hydrocarbons with silicalite zeolite", J. Chem. Soc. Faraday Trans., 1996, vol. 92, pp. 2499-2502.
Minceva et al., "Modeling and simulation of a simulated moving bed for the separation of p-xylene", Ind. Eng. Chem. Res., 2002, vol. 41, pp. 3454-3461.
Minceva et al., "Understanding and revamping of industrial scale SMB units for p-xylene separation", AIChE Journal, 2007, vol. 53, pp. 138-149.
Pais et al., "Chiral separation by SMB chromatography", Sep. Pur. Tech., 2000, vol. 20, pp. 67-77.
Rajendran et al., "Simulated moving bed chromatography for the separation of enantiomers", J. Chrom. A, 2009, vol. 1216, pp. 709-738.
Silva et al., "Fixed-bed adsorption of aromatic C8 isomers: Breakthrough experiments, modeling and simulation", 2012, vol. 90, pp. 246-256.
Silva et al., "Modeling and simulation of an industrial-scale parex process", AIChE Journal, 2015, vol. 61, pp. 1345-1363.
Tokay et al., "Nanopaiticle silicalite-1 crystallization from clear solutions: Nucleation", Micropor. Mesopor. Mat., 2009, vol. 118, pp. 143-151.
Ruthven et al., "Counter-Current and Simulated Counter-Current Adsorption Separation Processes", Chem. Eng. Sci., 1989, vol. 44, pp. 1011-1038.

* cited by examiner

*Primary Examiner* — Thuan D Dang
(74) *Attorney, Agent, or Firm* — Kristina Okafor

(57) ABSTRACT

In a process for separating one or more 3,3'-, 3,4'- and 4,4'-dimethyl biphenyl isomers, a feed comprising the isomers is contacted with an adsorbent containing a zeolite having a largest diffuse along dimension of at least 4 Angstroms. The adsorbents provide selective adsorption of 4,4'-dimethyl biphenyl.

25 Claims, 7 Drawing Sheets

PROCESSES FOR SEPARATING DIMETHYL BIPHENYL ISOMERS USING ZEOLITE ADSORBENTS

FIELD

The present disclosure relates to processes for separating one or more of 3,3'-, 3,4'- and 4,4'-dimethyl biphenyl (DMBP) isomers from mixtures comprising the isomers. The disclosure also relates to processes for modifying the relative amounts of the DMBP isomers in such mixtures. The processes are facilitated by zeolite adsorbents.

BACKGROUND

Dimethyl biphenyl (DMBP) compounds are useful intermediates in the production of a variety of commercially valuable products, including polyesters and plasticizers for PVC and other polymer compositions. DMBP compounds can be readily converted to an ester plasticizer by a process comprising oxidation of the DMBP to produce the corresponding mono- or dicarboxylic acid followed by esterification with a long chain alcohol.

For example, 4,4'-biphenyl-dicarboxylic acid, optionally together with 3,4'-biphenyl dicarboxylic acid, is a potential precursor, either alone or as a modifier for polyethylene terephthalate (PET), in the production of polyester fibers, engineering plastics, liquid crystal polymers for electronic and mechanical devices, and films with high heat resistance and strength.

Processes to produce DMBP compounds generally yield a mixture of all six DMBP isomers, namely 2,2'-, 2,3'-, 2,4'-, 3,3'-, 3,4'- and 4,4'-DMBP (see, for example, International Patent Application Publication No. WO 2015/112252).

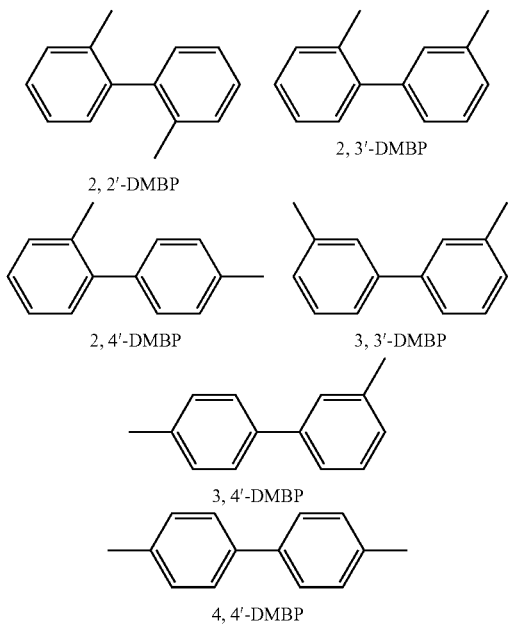

However, for certain applications, it is desirable to maximize the purity of individual isomers, particularly the 3,3'-, 3,4'- and 4,4'-isomers.

Based on boiling point differences it is possible to separate the 3,3'-, 3,4'- and 4,4'-isomers from the 2,X'-isomers, where X=2, 3 or 4, utilizing, for example, fractional distillation. However, separation of the 3,3'-, 3,4'- and 4,4'-isomers from each other based on boiling point is more challenging, particularly separation of the 3,4'-isomer from the 4,4'-isomer which have very close boiling points (see Table 1 below).

TABLE 1

| Isomer | Normal Boiling Point (° C.) | Fusion Temperature (° C.) |
| --- | --- | --- |
| 2,2' | 261 | 19 |
| 2,3' | 272 | |
| 2,4' | 275 | −24 |
| 3,3' | 289 | 8 |
| 3,4' | 293 | 11 |
| 4,4' | 296 | 115 |

Further, based on heat of fusion differences it is in principle possible to effect separation of 3,3'-, 3,4'- and 4,4'-isomers via crystallization. However, because the relative proportions of some of these isomers in a given mixture may be small separation via crystallization may not be commercially attractive.

It is known that certain adsorbents, for example zeolites, can be used to separate individual hydrocarbons from mixtures thereof. Adsorptive separation may be useful where the components to be separated have similar physical properties such as boiling point and melting points. For example, utilizing zeolites it is possible to selectively separate a predetermined xylene from a mixture of xylene isomers. See, for example, United States Patent Application Publication No. 2009/0326310 and references therein.

In view of the above it would be desirable to provide alternative processes for the separation of 3,3'-, 3,4'- and 4,4'-DMBP isomers, particularly processes that may be amenable to commercial implementation.

The reference in this specification to any prior publication (or information derived from it), or to any matter which is known, is not, and should not be taken as an acknowledgement or admission or any form of suggestion that that prior publication (or information derived from it) or known matter forms part of the common general knowledge in the field of endeavour to which this specification relates.

SUMMARY

In a first aspect of the present disclosure there is provided a process for separating one or more of the dimethyl biphenyl (DMBP) isomers, 3,3'-DMBP, 3,4'-DMBP and/or 4,4'-DMBP from a mixture comprising two or more of said isomers, the process comprising a step of contacting said mixture with an adsorbent comprising at least one zeolite, wherein said zeolite has a largest diffuse along dimension of at least about 4 Angstroms (Å).

In a second aspect of the present disclosure there is provided a process for modifying the relative amounts of the dimethyl biphenyl (DMBP) isomers, 3,3'-DMBP, 3,4'-DMBP and/or 4,4'-DMBP in a mixture comprising two or more of said isomers, the process comprising a step of contacting said mixture with an adsorbent comprising at least one zeolite, wherein said zeolite has a largest diffuse along dimension of at least about 4 Angstroms (Å).

As used herein the term 'zeolite', as well as encompassing aluminosilicate materials, also encompasses zeolite analogues where one or more of the framework aluminum or silicon atoms are replaced by another atom, such as, for example, boron, gallium, germanium, magnesium, titanium, phosphorus, nitrogen or sulfur.

As used herein the term 'largest diffuse along dimension' refers to a measure of the largest dimension of a zeolite channel system based on the diameter of the largest possible free-sphere that can diffuse along dimensions a, b or c of a zeolite channel and which are computed geometrically by Delaunay triangulation as detailed in: "A geometric solution to the largest-free-sphere problem in zeolite frameworks", M.D. Foster, I. Rivin, M. M. J. Treacy and O. Delgado Friedrichs, *Micropor. Mesopor. Mat.*, 90, 32-38, 2006.

In both the foregoing aspects of the present disclosure the largest diffuse along dimension of the zeolite may be at least about 4.5 Å, or at least about 5.0 Å, or at least about 5.5 Å, or at least about 6.0 Å, or at least about 6.5 Å, or at least about 7.0 Å.

In both the foregoing aspects of the present disclosure the largest diffuse along dimension of the zeolite may be between about 4.0 Å and about 8.0 Å, or between about 4.5 Å and about 8.0 Å, or between about 5.0 Å and about 8.0 Å, or between about 5.5 Å and about 8.0 Å, or between about 6.0 Å and about 8.0 Å, or between about 6.5 Å and about 8.0 Å.

Embodiments of the present disclosure are directed to processes for separating 4,4'-DMBP from a mixture comprising 3,3'-DMBP, 3,4'-DMBP and 4,4'-DMBP. The mixture may be contacted under adsorption conditions with an adsorbent comprising, for example, ZSM-5 zeolite. Aspects of the disclosure are associated with the discovery that 'nano zeolites', for example, 'nano ZSM-5' (i.e., nano-size zeolite ZSM-5 crystallites having an average crystallite size below 1000 nm) provides highly advantageous performance characteristics when incorporated into adsorbents used in the adsorptive separation of 4,4'-DMBP. In particular, the mass transfer rate of 4,4'-DMBP into the zeolite pores is significantly greater, relative to zeolites synthesized according to conventional methods which typically have an average crystallite size on the order of 1-5 microns.

This increase in mass transfer rate in turn reduces the amount of adsorbent required to obtain a given flow rate of product (e.g., an extract product stream) from a given feed stream, for any desired set of performance parameters (e.g., 4,4'-DMBP purity and recovery). Process economics are therefore improved.

Adsorbents comprising the 'nano-zeolites, for example 'nano ZSM-5', may have greater 4,4'-DMBP capacity with comparable selectivity, relative to zeolite adsorbents with larger average zeolite crystallite sizes.

In both the forgoing aspects the average crystallite size of the zeolite may be less than about 5000 nm, or less than about 2000 nm, or less than about 1000 nm, or less than about 500 nm, or less than about 200 nm, or less than about 100 nm, or less than about 50 nm.

In both the forgoing aspects the average crystallite size of the zeolite may be from about 1 to about 5000 nm, or from about 1 to about 2000 nm, or from about 1 to about 1000 nm, or from about 5 to about 500 nm, or from about 10 to about 100 nm.

In both the foregoing aspects of the present disclosure the zeolite structure type may comprise BEA, FAU, MFI, MEL, MTW, MOR, LTL, EMT, FER, MAZ, MEI, TON, MWW, EUO, MFS, IMF, MRE, ITN, MTT, MSE or IWV.

In both the foregoing aspects of the present disclosure the zeolite may comprise a 12-ring zeolite, an 11-ring zeolite or a 10-ring zeolite.

In both the foregoing aspects the zeolite may comprise a ZSM-5, or a ZSM-11, or a ZSM-57, or a ZSM-48 or a ZSM-12 type zeolite.

In both the foregoing aspects the zeolite may be a dealuminated zeolite or an aluminum free zeolite such as silicalite. In both the foregoing aspects the Si/Al ratio of the zeolite may be greater than about 10, or greater than about 20, or greater than about 50, or greater than about 100, or greater than about 150, or greater than about 200. In any of the foregoing aspects the Si/Al ratio of the zeolite may be between about 10 and about 300, or between about 15 and about 250.

In some embodiments the zeolite may be substantially free of alkali metal cations and alkaline earth metal cations. The alkali metal cation and alkaline earth metal cation content may, in combination, be less than about 0.1 wt. %, or less than about 0.075 wt. %, or less than about 0.05 wt. %.

The mixtures of 3,3'-DMBP, 3,4'-DMBP and 4,4'-DMBP isomers utilized in the presently disclosed processes may further comprise one or more solvents. A wide range of solvents are contemplated. Preferred solvents include saturated hydrocarbons and aromatic hydrocarbons.

Aspects of the present disclosure are based on the surprising discovery that solvent choice has an impact on the separation of the 3,3'-DMBP, 3,4'-DMBP and 4,4'-DMBP isomers.

In some embodiments of the processes of the present disclosure the degree of separation of the 3,3'-DMBP, 3,4'-DMBP and 4,4'-DMBP isomers may be based on the kinetic diameter of the solvent. The kinetic diameter may be derived from a spherical model or a smallest ellipsoid model. In other embodiments the degree of separation may be based on the polarity of the solvent. In yet other embodiments the degree of separation may be based on both the kinetic diameter of the solvent and its polarity. Accordingly, solvents which are bulkier (generally a larger kinetic diameter) may afford improved separation of the isomers, however this effect may be modulated by solvent polarity. Generally, single ring aromatic solvents such as benzene adsorb to the zeolite more strongly that saturated solvents.

Without wishing to be bound by theory it is believed that there is a tertiary interaction involving the DMBP isomers, the solvent and the zeolite pores which impact on the efficacy of selective adsorption of one or more of the DMBP isomers. Preferred solvents are those which do not significantly compete with a particular DMBP isomer in respect of adsorption into the pores of the zeolite. Accordingly, due to their higher polarity, aromatic solvents are more likely to be bulkier relative to aliphatic solvents in order to achieve comparable adsorption of DMBP.

The kinetic diameters of various solvents of relevance to the present disclosure are shown in Table 2 below (see J. Chem. Soc., Faraday Trans., 1996, 92, 2499-2502 and J. Phys. Chem, 1996, 100, 7676-7679).

TABLE 2

| Solvent | Kinetic Diameter (Å) |
| --- | --- |
| iso-octane | 6.2 |
| tri-isopropyl benzene | 8.5 |
| toluene | 5.9 |
| p-xylene | 5.9 |
| m-xylene | 6.8 |
| mesitylene | 7.5 |

In some embodiments the solvent comprises a saturated organic solvent wherein the kinetic diameter of the solvent is greater than about 4.5 Å, or greater than about 5.0 Å, or greater than about 5.5 Å, or greater than about 6.0 Å.

In some embodiments the solvent comprises an aromatic organic solvent wherein the kinetic diameter of the solvent is greater than about 6.0 Å, or greater than about 6.5 Å, or greater than about 7.0 Å, or greater than about 7.5 Å.

In some embodiments the solvent kinetic diameter is greater than the largest diffuse along dimension of the zeolite.

In some embodiments the solvent kinetic diameter is greater than the largest diffuse along dimension of the zeolite by at least 0.5 Å, or at least 1.0 Å, or at least 1.5 Å, or at least 2.0 Å.

In some embodiments the processes disclosed herein comprise separating 4,4'-DMBP from a mixture comprising two or more of 3,3'-DMBP, 3,4'-DMBP and 4,4'-DMBP.

In some embodiments the processes disclosed herein comprise modifying the relative amounts of 3,3'-DMBP, 3,4'-DMBP and/or 4,4'-DMBP in a mixture comprising 3,3'-DMBP, 3,4'-DMBP and 4,4'-DMBP.

In some embodiments the processes disclosed herein comprise reducing the relative amount of 4,4'-DMBP in a mixture comprising two or more of 3,3'-DMBP, 3,4'-DMBP and 4,4'-DMBP.

In one embodiment the process comprises separating 4,4'-DMBP from a mixture comprising two or more of 3,3'-DMBP, 3,4'-DMBP and 4,4'-DMBP, wherein the zeolite has a largest diffuse along dimension of at least about 4 Angstroms (Å).

In one embodiment the process comprises separating 4,4'-DMBP from a mixture comprising 3,3'-DMBP, 3,4'-DMBP and 4,4'-DMBP, wherein the zeolite has a largest diffuse along dimension of at least about 4 Angstroms (Å), and wherein the solvent is a saturated organic solvent having a kinetic diameter greater than about 4.5 Å.

In another embodiment the process comprises separating 4,4'-DMBP from a mixture comprising 3,3'-DMBP, 3,4'-DMBP and 4,4'-DMBP, wherein the zeolite has a largest diffuse along dimension of at least about 4 Angstroms (Å), and wherein the solvent is an aromatic organic solvent having a kinetic diameter greater than about 6.0 Å.

In another embodiment the process comprises separating 4,4'-DMBP from a mixture comprising 3,3'-DMBP, 3,4'-DMBP and 4,4'-DMBP, wherein the zeolite has a largest diffuse along dimension of at least about 4 Angstroms (Å), and wherein the average crystallite size of the zeolite is from about 10 to about 100 nm.

In another embodiment the process comprises separating 4,4'-DMBP from a mixture comprising 3,3'-DMBP, 3,4'-DMBP and 4,4'-DMBP, wherein the zeolite has a largest diffuse along dimension of at least about 4 Angstroms (Å), wherein the average crystallite size of the zeolite is from about 10 to about 100 nm, and wherein the solvent is a saturated organic solvent having a kinetic diameter greater than about 4.5 Å.

In another embodiment the process comprises separating 4,4'-DMBP from a mixture comprising 3,3'-DMBP, 3,4'-DMBP and 4,4'-DMBP, wherein the zeolite has a largest diffuse along dimension of at least about 4 Angstroms (Å), wherein the average crystallite size of the zeolite is from about 10 to about 100 nm, and wherein the solvent is a an aromatic organic solvent having a kinetic diameter greater than about 6.0 Å.

In another embodiment the process comprises separating 4,4'-DMBP from a mixture comprising 3,3'-DMBP, 3,4'- DMBP and 4,4'-DMBP, wherein the zeolite has a largest diffuse along dimension of at least about 4 Angstroms (Å), wherein the average crystallite size of the zeolite is from about 10 to about 100 nm, and wherein the solvent comprises iso-octane, m-xylene, 1,2,4-trimethylbenzene, 1,3,5-trimethylbenzene, 1,4-diisopropylbenzene, 3,3'-DMBP, 1,3,5-triisopropylbenzene or combinations thereof.

The processes of the present disclosure may afford pure, substantially pure or enriched individual DMBP isomers. Purities of 3,3'-DMBP, 3,4'-DMBP and 4,4'-DMBP may, independently, be greater that 90 wt. %, or greater than 95 wt. %, or greater than 96 wt. %, or greater than 97 wt. % or greater than 98 wt. %, or greater than 99 wt. % or greater than 99.5 wt. %, or greater than 99.9 wt. %.

In some embodiments the solvent heat of adsorption is less than a DMBP isomer heat of adsorption.

The processes may be performed over a wide range of temperatures. Preferably the temperature is above about 20° C. or above about 115° C. The temperature may be between about 20° C. and about 300° C., or between about 20° C. and about 250° C., or between about 20° C. and about 200° C.

The processes may be performed in batch or continuous mode.

The contact time between the zeolite and the DMBP mixture may be between a few seconds and several hours, or between a few minutes and several hours, or between about 0.5 hours and about 10 hours, or between about 0.5 hours and about 5 hours.

In some embodiments mixtures of solvents may be utilized to facilitate separation of the DMBP isomers. In other embodiments solvent gradients may be utilized to improve separation.

In some embodiments, the solvent or solvents used in the adsorptive separations may have a boiling point that is substantially lower than those of the DMBP isomers so as to facilitate separation of the solvents from the DMPB isomers by, for example, fractional distillation. In other embodiments a solvent of higher boiling point than those of the DMBP isomers may be utilized. In some embodiments both higher and lower boiling solvents may be used. In some embodiments the difference between the boiling point of the solvent or solvents and the boiling point of any one of the 3,3'-DMBP, 3,4'-DMBP and 4,4'-DMBP isomers is greater than about 100° C., or greater than about 75° C., or greater than about 50° C., or greater than about 25° C.

DETAILED DESCRIPTION OF THE EMBODIMENTS

Figure 1:
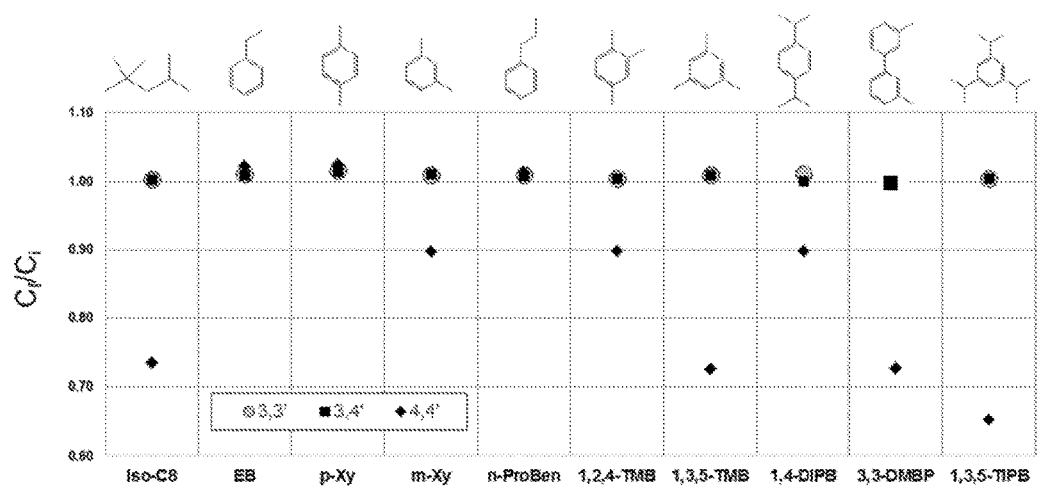
FIG. 1 is a plot of concentration changes (Cf/Ci) in the liquid phase after adsorption of DMBP isomers on ZSM-5 zeolite using various solvents at room temperature.

Before the present processes are disclosed and described, it is to be understood that unless otherwise indicated this disclosure is not limited to specific compositions, components, processes, or the like, as such may vary, unless otherwise specified. It is also to be understood that the terminology used herein is for the purpose of describing particular embodiments only and is not intended to be limiting.

It must also be noted that, as used in the specification and the appended claims, the singular forms 'a', 'an' and 'the' include plural referents unless otherwise specified. Thus, for example, reference to 'a solvent' may include more than one solvent, and the like.

Throughout this specification, use of the terms "comprises" or "comprising" or grammatical variations thereon shall be taken to specify the presence of stated features, integers, steps or components but does not preclude the presence or addition of one or more other features, integers, steps, components or groups thereof not specifically mentioned.

Disclosed herein are advantageous compositions and process for the separation of 3,3'-DMBP, 3,4'-DMBP and 4,4'-DMBP isomers. The compositions and processes are based on zeolite adsorbents.

In some embodiments the adsorbent is at least one zeolite, wherein said zeolite has a largest diffuse along dimension of at least about 4 Angstroms (Å).

In some embodiments, the zeolite is substantially free of alkali metal cations and alkaline earth metal cations.

Preferably the largest diffuse along dimension of the zeolite is at least about 4.5 Å, or at least about 5.0 Å, or at least about 5.5 Å, or at least about 6.0 Å, or at least about 6.5 Å, or at least about 7.0 Å.

Preferably the largest diffuse along dimension of the zeolite is between about 4.0 Å and about 8.0 Å, or between about 4.5 Å and about 8.0 Å, or between about 5.0 Å and about 8.0 Å, or between about 5.5 Å and about 8.0 Å, or between about 6.0 Å and about 8.0 Å, or between about 6.5 Å and about 8.0 Å.

Numerous zeolite structural types are useful as selective adsorbents in the present processes, for example, BEA, FAU, MFI, MEL, MTW, MOR, LTL, EMT, FER, MAZ, MEI, TON, MWW, EUO, MFS, IMF, MRE, ITN, MTT, MSE and IWV.

Preferred zeolites comprise a 12-ring zeolite, an 11-ring zeolite or a 10-ring zeolite.

It has also been discovered that the crystallite size of the zeolite may improve the adsorptive ability.

The average crystallite size of the zeolite may be less than about 5000 nm, or less than about 2000 nm, or less than about 1000 nm, or less than about 500 nm, or less than about 200 nm, or less than about 100 nm, or less than about 50 nm.

The average crystallite size of the zeolite may be from about 1 to about 5000 nm, or from about 1 to about 2000 nm, or from about 1 to about 1000 nm, or from about 5 to about 500 nm, or from about 10 to about 100 nm.

The average crystallite size of the zeolite may be from about 500 to about 5000 nm, or from about 1000 to about 5000 nm, or from about 1000 to about 4000 nm.

Both the natural and synthetic zeolites or zeolite analogues may be used as adsorbents in the processes of the present disclosure. An example of a zeolite encompassed by the present disclosure for use as an adsorbent includes aluminosilicate cage structures in which the alumina and silica tetrahedra are intimately connected with each other in an open three-dimensional crystalline network. The tetrahedra are cross-linked by the sharing of oxygen atoms. The spaces between the tetrahedra are occupied by water molecules prior to dehydration. Subsequent partial or total dehydration results in crystals interlaced with channels of molecular dimensions. In the hydrated form, the crystalline aluminosilicates may be represented by the formula

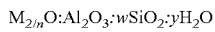

$$M_{2/n}O:Al_2O_3:wSiO_2:yH_2O$$

where M is a metal cation which balances the electrovalence of the tetrahedra, n represents the valence of the metal cation, w represents the mols of $SiO_2$ and Y, the mols of water. The metal cations may be any one of a number of cations such as for example the alkali metal cations or the alkaline earth cations or other selected metal cations.

Zeolites which find use as adsorbents in the process of the present disclosure may possess relatively well-defined pore structure. The exact zeolite type is generally referred to by the particular silica-alumina ratio and the pore dimensions of the cage structures. For example, the faujasites are commonly represented as type X and type Y aluminosilicates and are defined by their varying silica to alumina ratios.

The solvent used in the adsorptive separations of the processes of the present disclosure is preferably a material that is separable from the mixture that is fed to the solid adsorbent. In desorbing the adsorbed component of the mixture, both the solvent and the desorbed component are removed from the adsorbent as a mixture, and without a method of separation of these two materials the purity of the adsorbed component of the feed would not be very high. Therefore, it is contemplated that a solvent that is of a different boiling range than the feed mixture fed to the solid adsorbent be used in this separation process. The use of a solvent of a differing boiling range would allow fractionation or other separation methods to be used to separate the selectively adsorbed feed component as a relatively pure product stream and allow recovery of the solvent for possible recycle in the process.

Solvents which can be used in the process of the present disclosure include, for example, iso-octane and mesitylene. Iso-octane and mesitylene have boiling points of 99 and 165° C. respectively, whereas 3,3'-DMBP, which is the lowest boiling DMBP isomer, boils at around 289° C.

The adsorbent can be contained in a single vessel where, through programmed flow into and out of the vessel, a separation of a desired DMBP isomer is effected. Swing bed operational techniques where a series of adsorbent vessels are available or simulated moving bed countercurrent operations may be used. In the latter method of operation the selection of a suitable solvent requires that it be capable of readily displacing a particular adsorbed DMBP isomer from the adsorbent.

In embodiments of the present disclosure the process of separating 4,4'-DMBP from a mixture comprising 3,3'-DMBP, 3,4'-DMBP and 4,4'-DMBP may comprise any one of the combinations of zeolite and solvent characteristics as in Table 3.

TABLE 3

| Zeolite type | Zeolite crystallite size | Largest diffuse along dimension | Solvent kinetic diameter (Å) | Solvent (Å) |
|---|---|---|---|---|
| ZSM-5 | 10-100 | at least 4 | >4.5 | Aliphatic |
| ZSM-5 | 10-100 | at least 4 | >5.0 | Aliphatic |
| ZSM-5 | 10-100 | at least 4 | >5.5 | Aliphatic |
| ZSM-5 | 10-100 | at least 4 | >6.0 | Aliphatic or aromatic |
| ZSM-5 | 10-100 | at least 4 | >6.5 | Aliphatic or aromatic |
| ZSM-5 | 10-100 | at least 4 | >7.0 | Aliphatic or aromatic |
| ZSM-5 | 10-100 | at least 5 | >5.5 | Aliphatic |
| ZSM-5 | 10-100 | at least 5 | >6.0 | Aliphatic or aromatic |
| ZSM-5 | 10-100 | at least 5 | >6.5 | Aliphatic or aromatic |
| ZSM-5 | 10-100 | at least 5 | >7.0 | Aliphatic or aromatic |
| ZSM-5 | 10-100 | at least 6 | >6.5 | Aliphatic or aromatic |
| ZSM-5 | 10-100 | at least 6 | >7.0 | Aliphatic or aromatic |

The disclosure will now be more particularly described with reference to the following examples and FIGS. 1 to 7.

Preparation of Nano-Crystallite Zeolites

The method of Tokay B., Nanoparticle silicalite-1 crystallization from clear solutions: Nucleation, Microporous and Mesoporous Materials, Volume 118, Issues 1-3, 2009, Pages 143-151, was followed. To a plastic beaker while stirring vigorously was added 146.64 g of distilled water to 57.96 g of tetrapropylammonium hydroxide (TPA-OH). Stirring was continued and 98.95 g of tetraethylorthosilicate (TEOS) was added to the mixture. This was allowed to stir covered (foil over top of beaker) for 4 hours. After 4 hours, the beaker was uncovered and the mixture allowed to stir for ~16 h. The mixture was then poured into 300 cc autoclave and heated to 90° C. at a rate of 0.5 C/min and held at a temperature of 90° C. for 70 h. The product was discharged from the autoclave and centrifuged. It was washed three times with water and centrifuged each time. The white crystalline product was dried in a drying oven at 100° C. overnight and then calcined in a calcination furnace by ramping to 600° C. at 5° C./min in air and holding at 600° C. overnight ~16 h. The product had a crystallite size of <100 nm as determined by scanning electron microscopy.

Batch Adsorption Experiments

Adsorbents were evaluated for isolation of 4,4'-dimethylbiphenyl (4,4'-DMBP) from isomeric mixtures utilizing batch experiments. The adsorbents were dried under vacuum at 220° C. The dried solid materials were placed in a vial along with the DMBP mixture solution. The DMBP mixture solution was prepared by diluting a mixture of the isomers comprising about 25% by weight 3,3'-isomer, 55% by weight 3,4'-isomer and 20% by weight 4,4'-isomer in different solvents. The total DMBP isomer content in the starting liquid phase was about 10% by weight. All the preparations were performed in an inert atmosphere dry box to minimize moisture exposure. The liquid/solid mixture was then agitated in a shaker at room temperature overnight (>16 hrs). The supernatant liquid phase was subsequently analyzed by gas chromatography (GC) to obtain the DMBP concentration. Solvents used were ACS grade or higher as available. DMBP isomer mixtures were either synthesized in house via methods described in, for example, WO 2015/112252, or prepared using purchased pure isomers.

Isolation of 4,4'-DMBP

FIG. 1 illustrates the results of batch adsorption experiments with various solvents and utilizing ZSM-5 zeolite having a crystallite size between 2 and 5 μm (2000 and 5000 nm) and a Si/Al ratio of 220. The sodium content was <0.03 wt. %. The solvents examined were iso-octane, ethylbenzene, p-xylene, m-xylene, n-propylbenzene, 1,2,4-trimethylbenzene (1,2,4-TMB), 1,3,5-trimethylbenzene (1,3,5-TMB), 1,4-diisopropylbenzene, 3,3-DMBP and 1,3,5-triisopropylbenzene. For each solvent the amount of each DMBP isomer adsorbed is shown. The smaller the value of Cf/Ci, the more of a particular isomer is adsorbed. Ci is the initial concentration in the liquid phase and Cf is the final concentration in the liquid phase. It is apparent that ZSM-5 selectively adsorbs 4,4'-DMBP from a mixture of the isomers and that the solvent choice causes different adsorption selectivity for 4,4'-DMBP. Significantly, none of the solvents showed any adsorption of the other two isomers. This indicates 3,3'- and 3,4'-DMBP are excluded from the pores of the zeolite, allowing isolation of 4,4'-DMBP from the mixture. It also illustrates the strong effect of the solvent on the quantity of 4,4'-DMBP adsorbed. Different solvents effect different degrees of adsorption. Bulkier solvent molecules, such as isooctane (2,2,4 trimethylpentane), mesitylene (1,3,5-trimethylbenzene), 1,4-diisopropylbenzene, and 1,3,5-triisopropylbenzene, result in more penetration of 4,4'-DMBP into the pores. Aromatic solvents with more branched alkyl chains (e.g. mesitylene and 1,2,4-trimethylbenzene) result in higher adsorption of 4,4'-DMBP than those substituted with linear alkyl chains (e.g. n-propylbenzene).

Figure 2:
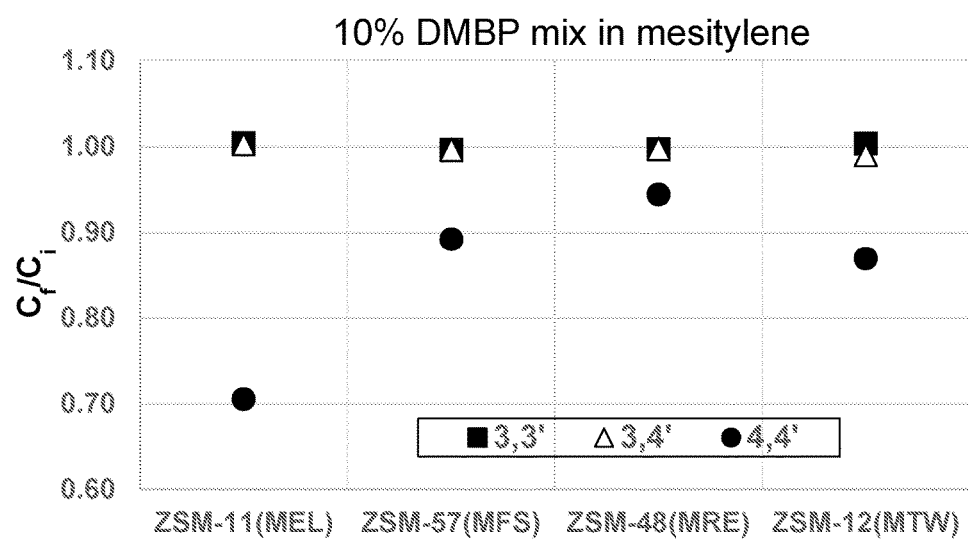
FIG. 2 is a plot of concentration changes (Cf/Ci) in the liquid phase after adsorption of DMBP isomers on various ZSM zeolites in mesitylene solvent at room temperature.

FIG. 2 is a plot of concentration changes (Cf/Ci) in the liquid phase after adsorption of DMBP isomers on various ZSM zeolite frameworks in mesitylene solvent at room temperature. In each case it can be seen that selective adsorption of the 4,4'-isomer occurred.

Influence of Crystallite Size

Figure 3:
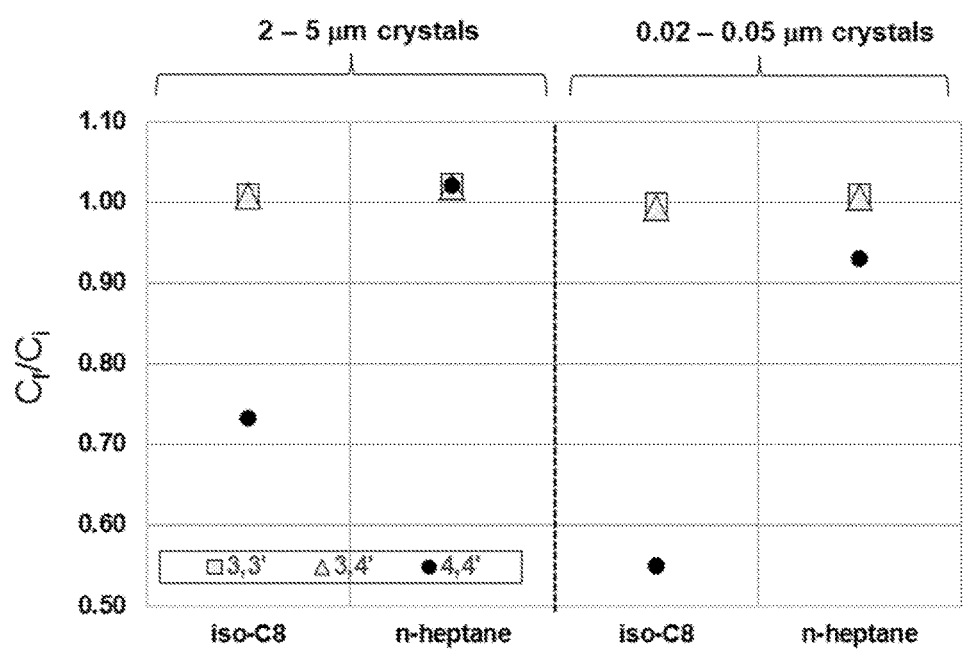
FIG. 3 is a plot of concentration changes (Cf/Ci) in the liquid phase after adsorption of DMBP isomers on two different sizes of ZSM-5 zeolite at room temperature.

FIG. 3 compares the effect of the size of the zeolite crystallites on 4,4'-DMBP adsorption. The batch experiment data in FIG. 3 indicates that the small crystallite ZSM-5 (MFI) zeolite gives higher 4,4'-DMBP loading than the larger crystallite zeolite. For example, with n-heptane as the solvent, there was no selective adsorption of 4,4'-DMBP observed with the large crystallite zeolite, whereas the small crystallite zeolite produced selective adsorption.

Continuous Breakthrough Experiments

A liquid chromatographic system was used for the breakthrough study of the adsorbents at elevated temperature. Adsorbents were packed into 4.6 mm ID×100 mm long stainless steel columns with 0.5 micron frits at each end. The adsorbents were dried at 300° C. for 1 hour in a flow of dry nitrogen. A packed column was equilibrated at 150° C. with a solvent (i.e. the mobile phase) prior to injection. The DMBP mixture solution (10 wt. %) was prepared in the same solvent as the mobile phase and introduced to a column through injection of a 6.6 ml pulse. The flow rate of solvent was set at 0.4 ml/min. Effluent from the column was collected in a fraction collector and the concentrations of DMBP in the fractions were determined by GC.

Figure 4:
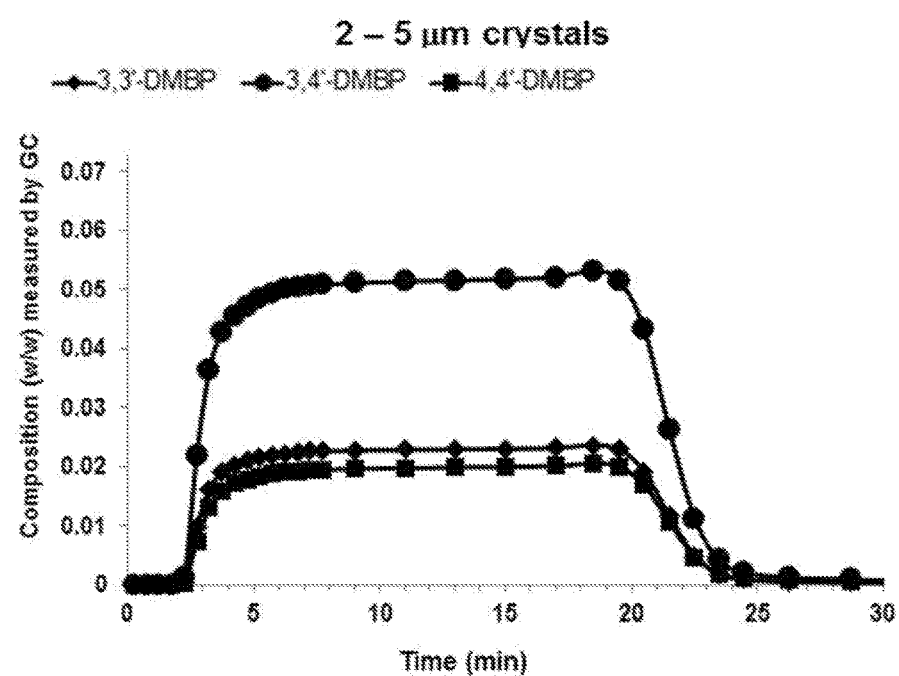
FIG. 4 illustrates the breakthrough curves for a mixture of 3,3'-DMBP, 3,4'-DMBP and 4,4'-DMBP in n-heptane solvent fed into a column containing ZSM-5 zeolite (2-5 μm crystallite size) at 150° C.
Figure 5:
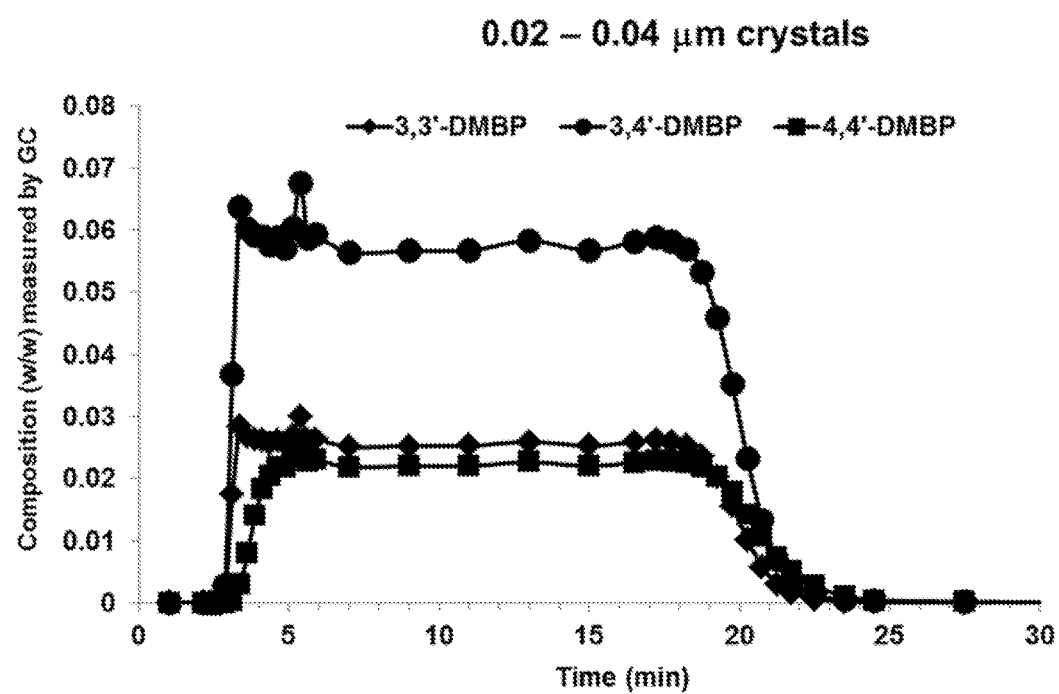
FIG. 5 illustrates the breakthrough curves for a mixture of 3,3'-DMBP, 3,4'-DMBP and 4,4'-DMBP in n-heptane solvent fed into a column containing ZSM-5 zeolite (0.02-0.04 μm crystallite size) at 150° C.

The effect of crystallite size was further tested by the breakthrough studies illustrated in FIGS. 4 and 5. A 3 ml pulse of 10 wt. % DMBP isomer mixture in n-heptane was introduced into columns containing large (2-5 micron) or small (20-40 nm) crystal size ZSM-5 zeolite. The same trend that the small crystallite size increases adsorption of the 4,4'-isomer was observed. With n-heptane as the mobile phase, all three isomers eluted at the same time from the large crystallite zeolite column (FIG. 3), and their breakthrough times indicate no retention of these isomers. However, the small crystallite ZSM-5 (MFI) zeolite (FIG. 4) resulted in adsorption of 4,4'-DMBP under the same conditions, as evidenced by the delayed breakthrough point.

Figure 6:
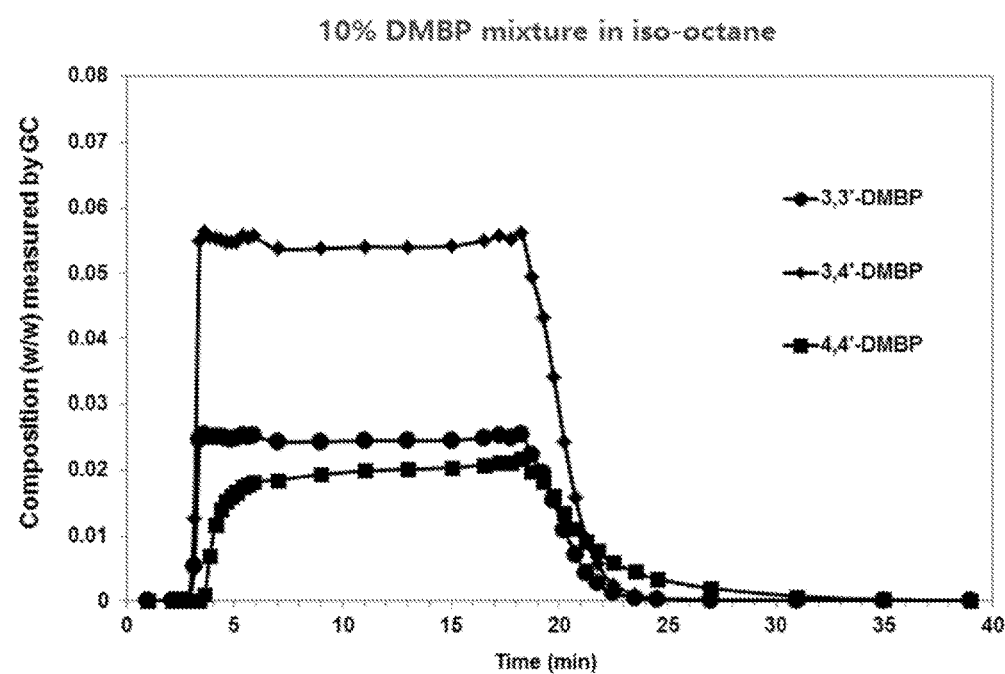
FIG. 6 illustrates the breakthrough curves for a mixture of 3,3'-DMBP, 3,4'-DMBP and 4,4'-DMBP in iso-octane solvent fed into a column containing ZSM-5 zeolite (0.02-0.04 µm crystallite size) at 150° C.
Figure 7:
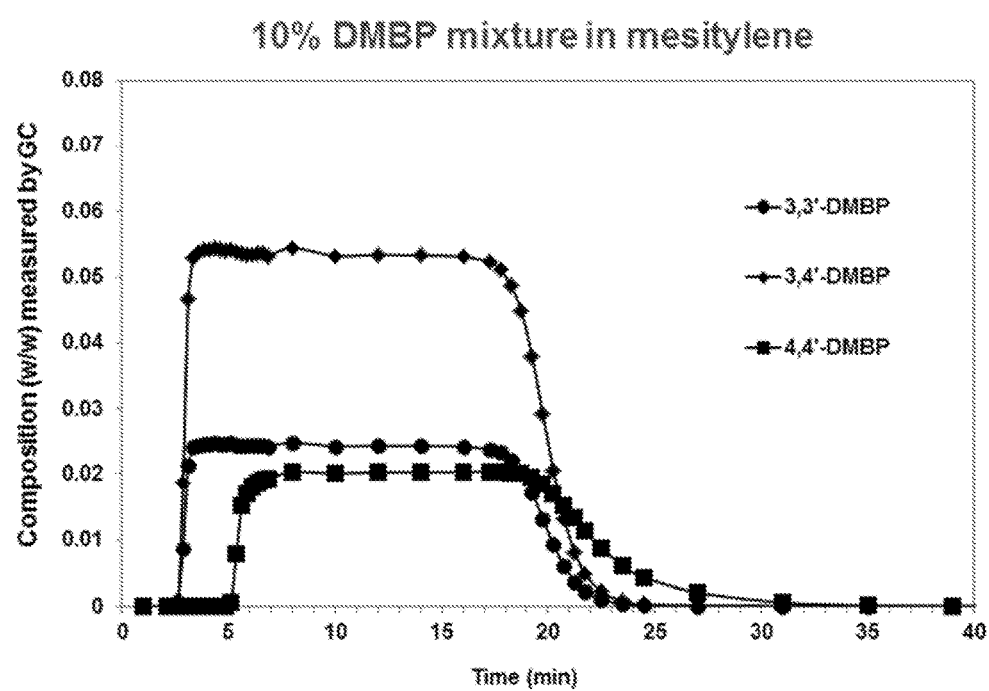
FIG. 7 illustrates the breakthrough curves for a mixture of 3,3'-DMBP, 3,4'-DMBP and 4,4'-DMBP in mesitylene solvent fed into a column containing ZSM-5 zeolite (0.02-0.04 µm crystallite size) at 150° C.

The effect of the solvent was also demonstrated by a breakthrough study at elevated temperature (150° C.). FIGS. 6 and 7 compare the breakthrough curves with different solvent systems using the larger crystallite size ZSM-5 zeolite and their impact on 4,4'-DMBP adsorption. Iso-octane and n-heptane are both paraffinic, but the branched bulkier iso-octane (FIG. 5) results in 4,4'-DMBP adsorption which is about two times higher than with n-heptane. The even bulkier mesitylene solvent (FIG. 7) increases the adsorption even more as compared to that with iso-octane. About three times higher 4,4'-DMBP adsorption was observed. Regardless of the solvents tested, the 3,3' and 3,4'-DMBP isomers were not adsorbed. The ratio of the total peak area under the curves is consistent with the initial composition of the feed, indicating the complete recovery of the DMBP isomers from the column. In the process, the non-adsorbed 3,3'- and 3,4'-DMBP can be removed from adsorbents and the adsorbed 4,4'-DMBP then recovered by desorption.

It is to be understood that while the present disclosure has been described in conjunction with the specific embodiments thereof, the foregoing description is intended to illustrate and not limit the scope of the disclosure. Other aspects, advantages and modifications will be apparent to those skilled in the art to which the disclosure pertains. Therefore, the above examples are put forth to provide those skilled in the art with a complete disclosure and description of how to use the disclosed processes, and are not intended to limit the scope of the disclosure.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited.

All documents cited herein are fully incorporated by reference for all jurisdictions in which such incorporation is permitted and to the extent such disclosure is consistent with the description of the present disclosure.

The invention claimed is:

1. A process for separating one or more of the dimethyl biphenyl (DMBP) isomers including 3,3'-DMBP, 3,4'-DMBP and/or 4,4'-DMBP from a mixture comprising two or more of said isomers, the process comprising a step of contacting said mixture with an adsorbent comprising at least one zeolite, wherein the zeolite structure type comprises BEA, FAU, MFI, MEL, MTW, MOR, LTL, EMT, FER, MAZ, MEI, TON, MWW, EUO, MFS, IMF, MRE, ITN, MTT, MSE or IWV, wherein said zeolite has a largest diffuse along dimension of at least about 4 Angstroms (Å) to separate one or more of the dimethyl biphenyl isomers from said mixture.

2. A process for modifying the relative amounts of the dimethyl biphenyl (DMBP) isomers including 3,3'-DMBP, 3,4'-DMBP and/or 4,4'-DMBP in a mixture comprising two or more of said isomers, the process comprising a step of contacting said mixture with an adsorbent comprising at least one zeolite, wherein the zeolite structure type comprises BEA, FAU, MFI, MEL, MTW, MOR, LTL, EMT, FER, MAZ, MEI, TON, MWW, EUO, MFS, IMF, MRE, ITN, MTT, MSE or IWV, wherein said zeolite has a largest diffuse along dimension of at least about 4 Angstroms (Å) to modify the relative amounts of the dimethyl biphenyl (DMBP) isomers in said mixture.

3. A process according to claim 1 or claim 2 wherein the largest diffuse along dimension of the zeolite is at least about 4.5 Å, or at least about 5.0 Å, or at least about 5.5 Å, or at least about 6.0 Å, or at least about 6.5 Å, or at least about 7.0 Å.

4. A process according to claim 1 or claim 2, wherein the largest diffuse along dimension of the zeolite is between about 4.0 Å and about 8.0 Å, or between about 4.5 Å and about 8.0 Å, or between about 5.0 Å and about 8.0 Å, or between about 5.5 Å and about 8.0 Å, or between about 6.0 Å and about 8.0 Å, or between about 6.5 Å and about 8.0 Å.

5. A process according to claim 1 or 2, wherein the average crystallite size of the zeolite is less than about 5000 nm, or less than about 2000 nm, or less than about 1000 nm, or less than about 500 nm, or less than about 200 nm, or less than about 100 nm, or less than about 50 nm.

6. A process according to claim 1 or 2, wherein the average crystallite size of the zeolite is from about 1 to about 5000 nm, or from about 1 to about 2000 nm, or from about 1 to about 1000 nm, or from about 5 to about 500 nm, or from about 10 to about 100 nm.

7. A process according to claim 1 or 2, wherein the zeolite comprises a 12-ring zeolite, an 11-ring zeolite or a 10-ring zeolite.

8. A process according to claim 1 or 2, wherein the zeolite comprises a ZSM-5, or ZSM-11, or ZSM-57, or ZSM-48 or ZSM-12 type zeolite.

9. A process according to claim 1 or 2, wherein the Si/Al ratio of the zeolite is greater than about 10, or greater than about 20, or greater than about 50, or greater than about 100, or greater than about 150, or greater than about 200.

10. A process according to claim 1 or 2, wherein the Si/Al ratio of the zeolite is between about 10 and about 300, or between about 15 and about 250.

11. A process according to claim 1 or 2, wherein the zeolite has a combined alkali metal cation and alkaline earth metal cation content of less than about 0.1 wt. %, or less than about 0.075 wt. %, or less than about 0.05 wt. %.

12. A process according to claim 1 or 2, wherein the zeolite is a silicalite.

13. A process according to claim 1 or 2, wherein the mixture of DMBP isomers further comprises one or more solvents.

14. A process according to claim 13, wherein the solvent is a saturated hydrocarbon, an aromatic hydrocarbon or mixtures thereof.

15. A process according to claim 13, wherein the solvent comprises an aliphatic hydrocarbon solvent having a kinetic diameter greater than about 4.5 Å, or greater than about 5.0 Å, or greater than about 5.5 Å, or greater than about 6.0 Å.

16. A process according to claim 13, wherein the solvent comprises an aromatic hydrocarbon solvent having a kinetic diameter greater than about 6.0 Å, or greater than about 6.5 Å, or greater than about 7.0 Å, or greater than about 7.5 Å.

17. A process according to claim 1, wherein the process comprises separating 4,4'-DMBP from a mixture comprising two or more of 3,3'-DMBP, 3,4'-DMBP and 4,4'-DMBP.

18. A process according to claim 13, wherein the process comprises separating 4,4'-DMBP from a mixture comprising 3,3'-DMBP, 3,4'-DMBP and 4,4'-DMBP and wherein the solvent comprises iso-octane, m-xylene, 1,2,4-trimethylbenzene, 1,3,5-trimethylbenzene, 1,4-diisopropylbenzene, 3,3'-DMBP, 1,3,5-triisopropylbenzene or combinations thereof.

19. A process according to claim 13, wherein the process comprises separating 4,4'-DMBP from a mixture comprising 3,3'-DMBP, 3,4'-DMBP and 4,4'-DMBP, wherein the solvent comprises iso-octane, m-xylene, 1,2,4-trimethylbenzene, 1,3,5-trimethylbenzene, 1,4-diisopropylbenzene, 3,3'-DMBP, 1,3,5-triisopropylbenzene or combinations thereof, and wherein the zeolite has an average crystalline size from about 10 to about 100 nm.

20. A process according to claim 13, wherein the process comprises separating 4,4'-DMBP from a mixture comprising 3,3'-DMBP, 3,4'-DMBP and 4,4'-DMBP, wherein the solvent comprises an aromatic solvent having a kinetic diameter greater than about 7 Å, and wherein the zeolite has an average crystallite size from about 10 to about 100 nm.

21. A process according to claim 13, wherein the process comprises separating 4,4'-DMBP from a mixture comprising 3,3'-DMBP, 3,4'-DMBP and 4,4'-DMBP, wherein the solvent comprises an aromatic solvent having a kinetic diameter greater than about 7 Å, and wherein the zeolite is a ZSM-5 zeolite having an average crystallite size from about 10 to about 100 nm.

22. A process according to claim 1 or 2, wherein the process is performed between about 20° C. and about 250° C.

23. A process according to claim 1 or 2, wherein the process is performed in batch or continuous mode.

24. A process according to claim 1 or 2, wherein the contact time between the zeolite and the DMBP mixture is between about 0.5 hours and about 5 hours.

25. A process according to claim 13, wherein the difference between the boiling point of the solvent or solvents and the boiling point of any one of the 3,3'-DMBP, 3,4'-DMBP and 4,4'-DMBP isomers is greater than about 100° C., or greater than about 75° C., or greater than about 50° C., or greater than about 25° C.

* * * * *